US012564467B1

(12) United States Patent
Iversen et al.

(10) Patent No.: US 12,564,467 B1
(45) Date of Patent: *Mar. 3, 2026

(54) FORM STABLE EXPANDABLE STENT

(71) Applicant: PMT Corporation, Chanhassen, MN (US)

(72) Inventors: Alfred A Iversen, Wayzata, MN (US); Matthew W Cree, Victoria, MN (US)

(73) Assignee: PMT Corporation, Chanhassen, MN (US)

( * ) Notice: Subject to any disclaimer, the term of this patent is extended or adjusted under 35 U.S.C. 154(b) by 390 days.

This patent is subject to a terminal disclaimer.

(21) Appl. No.: 18/379,037

(22) Filed: Oct. 11, 2023

Related U.S. Application Data

(63) Continuation-in-part of application No. 17/206,414, filed on Mar. 19, 2021, now Pat. No. 11,806,195.

(60) Provisional application No. 62/993,931, filed on Mar. 24, 2020.

(51) Int. Cl.
| | |
|---|---|
| *A61B 90/00* | (2016.01) |
| *A61M 29/02* | (2006.01) |
| *A61F 2/82* | (2013.01) |
| *A61M 3/02* | (2006.01) |

(52) U.S. Cl.
CPC ...... *A61B 90/02* (2016.02); *A61B 2560/0406* (2013.01); *A61F 2/82* (2013.01); *A61M 3/0283* (2013.01); *A61M 29/02* (2013.01)

(58) Field of Classification Search
CPC ... A61B 90/02; A61F 2/82; A61F 2/04; A61F 2/004; A61F 2/12; A61M 29/00; A61M 29/02; A61M 2210/1475; A61M 3/0283
See application file for complete search history.

(56) References Cited

U.S. PATENT DOCUMENTS

2013/0138134 A1*  5/2013  Elman .............. A61M 25/0026
606/193

* cited by examiner

*Primary Examiner* — Katherine M Rodjom
(74) *Attorney, Agent, or Firm* — Eggink & Eggink; Anthony G. Eggink; Katrina M. Eggink

(57) ABSTRACT
A form stable expandable stent and tissue expander assembly having a sealed outer shell body forming an internal chamber. A form stability member may be provided within the internal chamber of the shell body. Drainage/irrigation tubing extend through the chamber of the shell body and a fill tube is provided in communication with the internal chamber of the outer shell and extends outwardly therefrom. Manipulation structures with handles and other cooperating fastening and removing elements may be provided for use with the expandable stent and tissue expander assemblies of the invention.

20 Claims, 9 Drawing Sheets

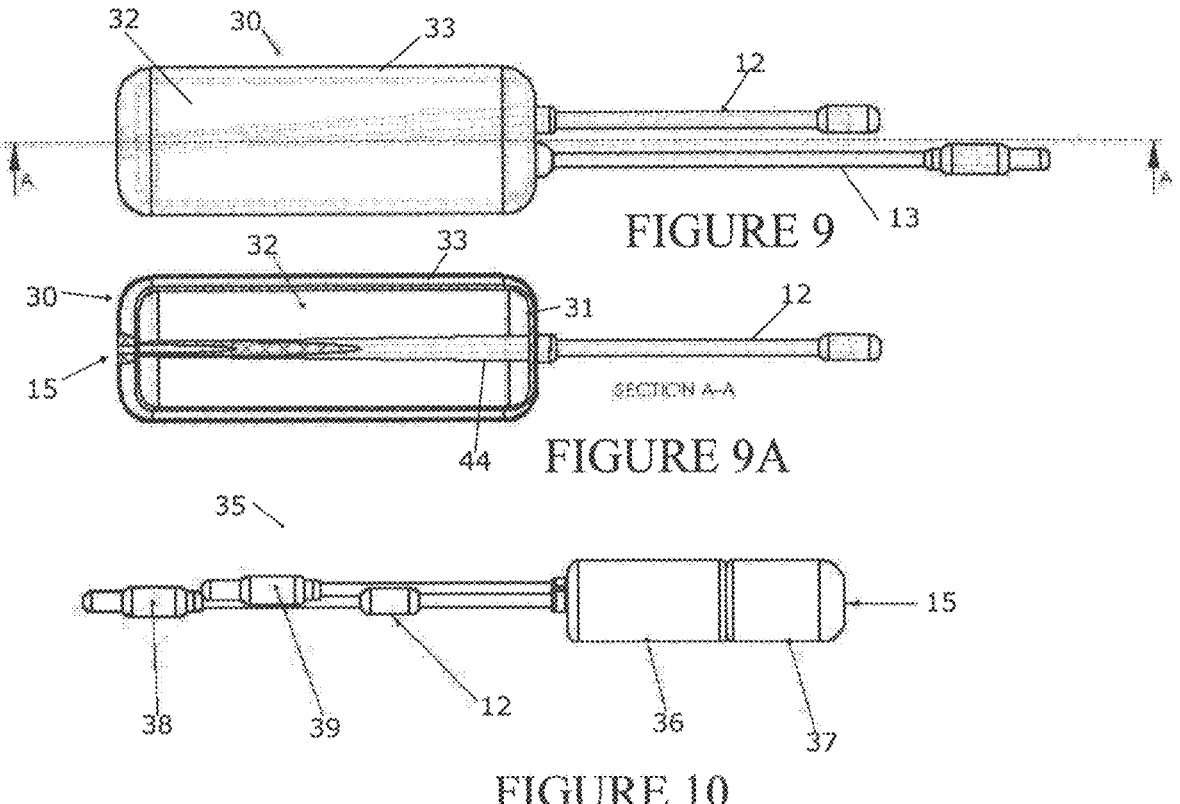
FIGURE 9
FIGURE 9A
FIGURE 10
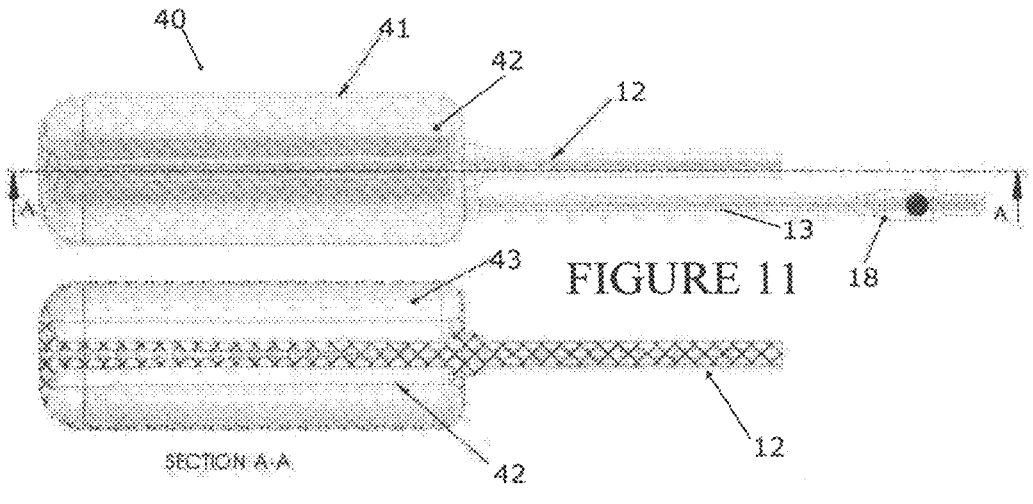
FIGURE 11
FIGURE 11A

DETAIL A VIEW

END VIEW

SECTION A

SECTION A-A VIEW

FORM STABLE EXPANDABLE STENT

This application is a continuation-in-part of U.S. patent application Ser. No. 17/206,414, filed on Mar. 19, 2021 and claims the benefit of U.S. Provisional Patent Application No. 62/993,931, filed on Mar. 24, 2020, and which is incorporated in its entirety by reference herein.

BACKGROUND OF THE INVENTION

The present invention relates generally to stents and particularly to expandable tissue stents utilized in the medical arts. More particularly, the invention relates to expandable stents and tissue expanders that are form stable.

The utilization of medical devices such as stents and tissue expanders in the medical arts continues to increase, however, presently available stent and tissue expander structures have inherent limitations when utilized for specified medical procedures. For example, prior art stents and tissue expanders typically have flexible bodies which limit the degree of physical manipulation required for the placement and use of these devices within specified confines of the human body. The form stable expandable tissue stents of the present invention overcome the limitations and related difficulties of these prior art stent and tissue expander devices.

The form stable expandable tissue stent of the invention may be used in the medical arts relating to treatments and procedures that require wound drainage and irrigation, and as a tissue graft stabilizer during and after surgeries, such as in reconstructive plastic surgery and neo-vaginal surgeries. Further uses of the invention include the use as an interoperative tissue expansion device, the use in tissue dilation during and after surgical procedures and as an expandable tissue dilator and expander. The tissue expander and expandable stents may be provided with integral wound drainage and irrigation tubing to provide wound drainage capabilities during and after surgical procedures and irrigation of the surgical site while the medical device is in place.

The form stable expandable stents and tissue expanders may be utilized in other procedures apparent to those skilled in the medical arts, for example, in patients with an internal surgical site requiring wound compression, internal tissue and organ expansion or retraction, internal cavity retraction after internal organ biopsy and as a tissue and organ shield during radiological patient exposure. Use in other medical art disciplines or procedures may also include: sacrocolpopexy, vaginal prolapse surgery, temporary control or reduction of postpartum hemorrhage after childbirth, pelvic organ prolapse, esophageal reconstruction, Nissen Fundoplication procedure using a form stable esophageal stent, colonic interposition surgery, colonic reconstruction and/or colonic resection.

The flexible and form stable expandable stents of the invention are easily inserted and allowed to expand into an interior void and utilized in surgical applications for patients with Mayer Rokitansky Kaster Hauser (MRKH) Syndrome, and in neovaginal creation, vaginal agenesis, transverse or longitudinal vaginal septum, vaginal stenosis due to postsurgical affects, tissue graft verses host affects, post Stevens Johnson stenosis, dilation of the cervix, dilation of the esophagus and colon surgical construction.

SUMMARY OF THE INVENTION

Form stable expandable stent and tissue expander assemblies for use in the medical arts. The assemblies have sealed expandable shells forming internal chambers. The shell structure may be constructed and arranged to provide a form stable assembly and/or a form stability member may be provided within the internal chamber of the expandable shell.

Drain/irrigation tubing are provided for extension through the expandable chamber and a fill tube having a ball valve, for example, is provided for fluid communication with the expandable chamber. The drain/irrigation tubing and the fill tube may be provided with a luer lock adapter.

The form stability member may comprise a thickened shell wall structure or a coiled foam structure positioned within the internal chamber of a shell structure. Other embodiments of form stability members and multiple internal chamber configurations are also provided by the expandable stent and tissue expander assemblies of the invention.

Cooperating elements including securement tabs, pull tabs and handle members with cooperating internal sleeve structures for moving and positioning the form stable expandable stent and tissue expander assemblies of the present invention are also disclosed.

The form stable expandable stent of the invention comprises an open cell foam or silicone structure positioned within a silicone shell that can be filled and expanded with a fluid such as air, saline or the like and which has a drainage and/or irrigation tube passing through the shell structure. The internally positioned open cell foam structure provides and improves the form stability of the expandable stent assembly to thereby ease the insertion of the device into the patient. Prior art devices, for example, tissue expanders or dilators consisting of silicone balloon structures filled with saline, have a tendency to fold over and buckle during insertion.

The form stable element comprised of coiled open cell foam structures, for example, may also be substituted by extruded or molded forms of soft rubber durometer silicone structures. The form stable structures provide evenly distributed compressive forces on the expandable stent shell to thereby stabilize the form of the device and the internal silicone structure further provides a simplified manufacturing process and a structure which is easier to sterilize.

The form stable expandable stent assembly may alternatively be molded of a thick exterior shell of soft durometer silicone rubber whereby the thick walls may eliminate the need for a foam interior while still allowing the stent device to be form stable when deflated, inflated and when slightly expanded.

The form stable expandable stent assembly may further have integrated multiple silicone shells and/or chambers within the same device body. The chambers may be filled at different pressures to allow for a semi-rigid device with a soft exterior, for example. The exterior surface of the stent shell may also have a distinctive texture that may be applied via silicone dip casting processes. The textured shell may reduce tissue adhesion to the stent body or capsulation while the tissue graft is healing and to thereby make the device removal easier and less painful to the patient.

Another embodiment of a semi-rigid device having a soft exterior may be provided by a reinforced drainage/irrigation tube, i.e., a Dacron mesh, wire mesh or like netting embedded in the silicone rubber. The reinforced tubing extending through the center of the device body may also be provided with gussets and ribbing vulcanized into the silicone rubber to likewise restrict the device body from bending and buckling. Additionally, multiple drain/irrigation tubing may also be integrated in the center of the form stable stent body to improve buckling resistance, while also improving cavity drainage while the patient is being irrigated. The irrigation tubing may be sized to maximize the fluid rate and pressure as the fluid is exiting the syringe. The separate drainage tube could be sized larger to allow the air in the cavity to escape during irrigation and to ensure full drainage of the cavity, thereby minimizing the risk of septic shock.

The drainage and irrigation tubing passes through the device body and is sealed from the internal fill chamber. The drainage and irrigation tube is structured for connection to a syringe or the like. The flush valve allows for wound irrigation and fluid extraction from the surgical site. The drainage and irrigation tube extends to the distal end of the stent body where multiple holes or apertures may be utilized to distribute the irrigation fluid and to aid in avoiding blockage from blood coagulate or clotting during fluid drainage.

The form stable expandable stent assembly may also incorporate features that improve the ability of the user to remove the device post-surgical dilation, for example. Reinforced tube and/or rigid eyelets may be provided to the silicone shell to allow for the application of tensible forces for device removal from the patient.

Flexible silicone tabs reinforced with Dacron netting may also be incorporated in the expandable stent assembly for suturing the stent device to the patient. The suture tabs may be utilized in the initial surgical procedure to limit device movement from the surgical pocket due to compressive tissue forces. The suture tabs may also aid the user in stent removal from the tissue pocket after healing. The reinforced tabs allow for the user to apply tensile forces to the stent body rather that the tubing which may cause damage and leakage.

These and other benefits of this invention will become clear from the following description by reference to the drawings.

BRIEF DESCRIPTION OF THE DRAWINGS

FIGS. 9 and 9A are lateral and sectional views, respectively, of another embodiment of the form stable expandable stent of the invention;

FIG. 10 is a lateral view of another embodiment of the form stable expandable stent of the invention;

FIGS. 11 and 11A are lateral and sectional views, respectively, of another embodiment of the form stable expandable stent of the invention;

DESCRIPTION OF THE PREFERRED EMBODIMENTS

The form stable expandable stent assembly of the invention generally comprises an expandable, flexible shell body having a form stability feature, a fill tube with a ball check valve and drainage and irrigation tubing integrated through the sealed expansion chamber of the shell body.

Figure 1:
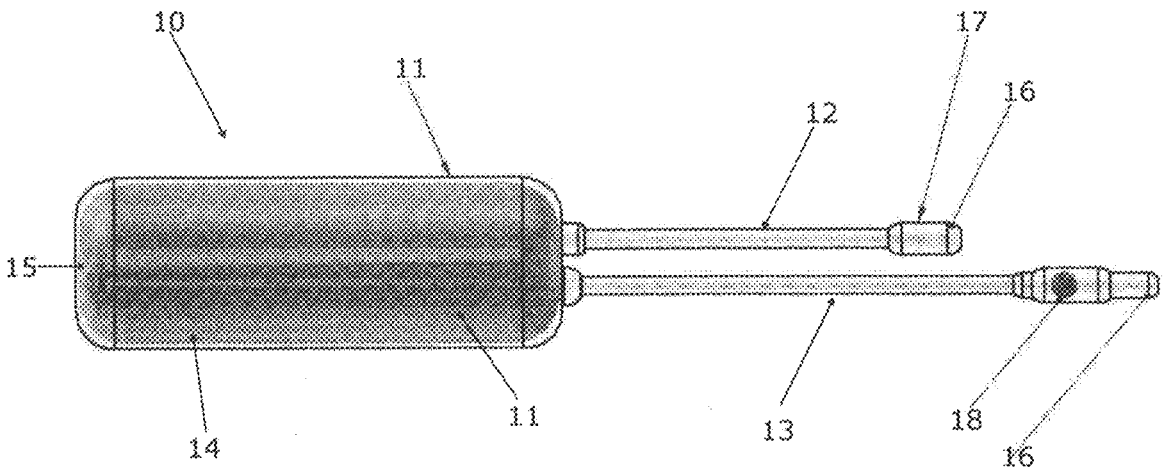
FIG. 1 is a lateral view of the form stable expandable tissue stent of the invention.
Figure 2:
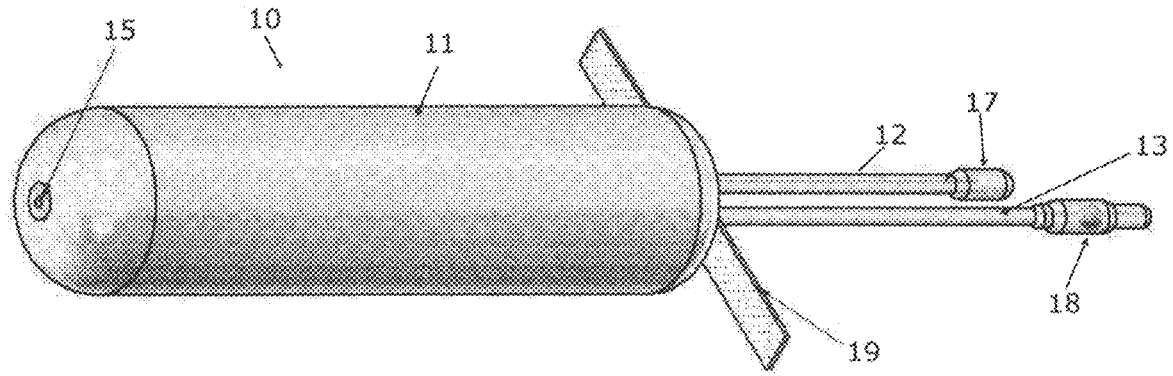
FIG. 2 is a lateral perspective view of an embodiment of the form expandable tissue stent of the invention.

Referring to FIGS. 1 and 2, a form stable expandable stent 10 is shown having a generally cylindrical body 11 defined by an expandable silicone shell having an open cell foam interior 14. The elongated cylindrical body 11 is shown to have round shouldered ends. A drainage and irrigation tube 12 having an irrigation valve 17 and luer lock adapter 16 at its terminal end is shown extending from one end of the stent body 11. A fill tube 13 having a ball valve 18 and a luer lock adapter 16 at its terminal end is further shown extending from the same end of the stent body 11. Luer lock style connectors are fluid fittings providing leak-free connections between male-taper and mating female part on medical instruments such as hypodermic syringe tips. A drainage and irrigation tube exit 15 is shown at the opposite end of the stent body 11. As shown in FIG. 2, reinforced silicone tabs 19 may be provided on the one end of the stent body 11 so that the expandable stent device 10 may be sutured in place and which also may be utilized for the removal of the device.

Figures 3, 4, 5:
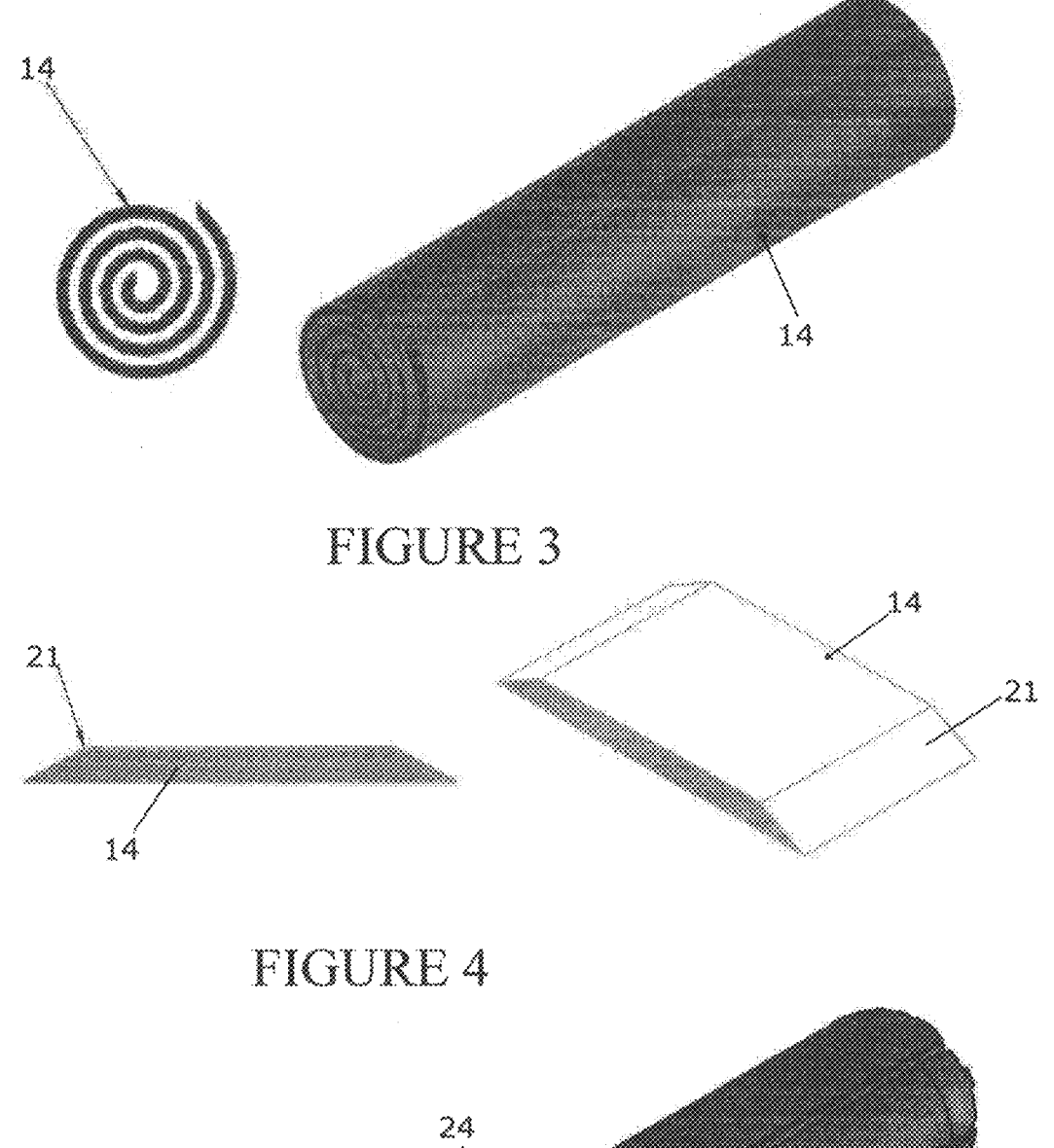
FIG. 3 is a perspective view of a foam structure utilized in the form stable expandable stent of the invention.
FIG. 4 is a perspective view of a foam structure of FIG. 3.
FIG. 5 is a perspective view of another embodiment of the foam structure of the invention.

Referring to FIGS. 3-5, alternate embodiments are shown of the interior element 14 that may be positioned within the cylindrical stent body 11 to provide the form stable structure of the expandable device 10. In FIG. 3, foam structure 14 is shown rolled into a spring coil configuration prior to insertion into the exterior shell body and is utilized to improve the rigidity of the device 10 during expansion and when in its expanded form. As shown in FIG. 4, the foam structure 14 is initially flat and has beveled end edges 21 to provide a smooth transition when in the spiraled or coiled configuration, as shown in FIG. 3, and to thereby reduce sharp transition areas which may result in pressure points to the stent device. The coiled foam structure 14 positioned within the internal chamber of the stent shell structure is capable of being compressed by the user to reduce the device diameter thereby providing easier insertion within a patient's cavity or surgical site. The manual compression creates a vacuum and subsequent positioning of the device, fluid entry into the device provides self expansion.

FIG. 5 shows a structurally extruded foam or rubber element 22 which may be utilized within the body shell of the stent device to provide form stability. The radial elements 24 provide an evenly distributed pressure and the overall structure further provides a reduced device body weight.

The shape and size of the shell body of the expandable device may vary and depend upon the patient's age and surgical requirements. Although the shape of an open cell foam structure 14 is shown to be a generally rolled rectilinear structure, other geometric shapes may also be cut or extruded to match the form or shape of the shell body. The open cell foam may be a polyurethane or a silicone material, for example, although a soft durometer silicone rubber composition may also be utilized.

As discussed further below, the shell body 11 of the expandable device may also be molded of a thick silicone rubber to provide a form stable stent assembly to eliminate the interior foam structure requirement. Further, the shell body 11 may be provided with multiple chambers and or shell structures, as further discussed below. The silicone rubber shell composition may also be formed of a polyurethane or like material. The tubing structures 12, 13 may be formed of silicone, polyurethane or like material.

The form stable stents utilizing a foam interior may have a silicone shell having a wall thickness ranging from 0.01 to 0.5 inches, for example. A form stable stent not utilizing a foam interior may have a thickened silicone wall ranging from 0.06 to 1.0 inches and having a durometer reading ranging from 10A to 90A shore, for example.

Figures 6, 7, 7A, 8:
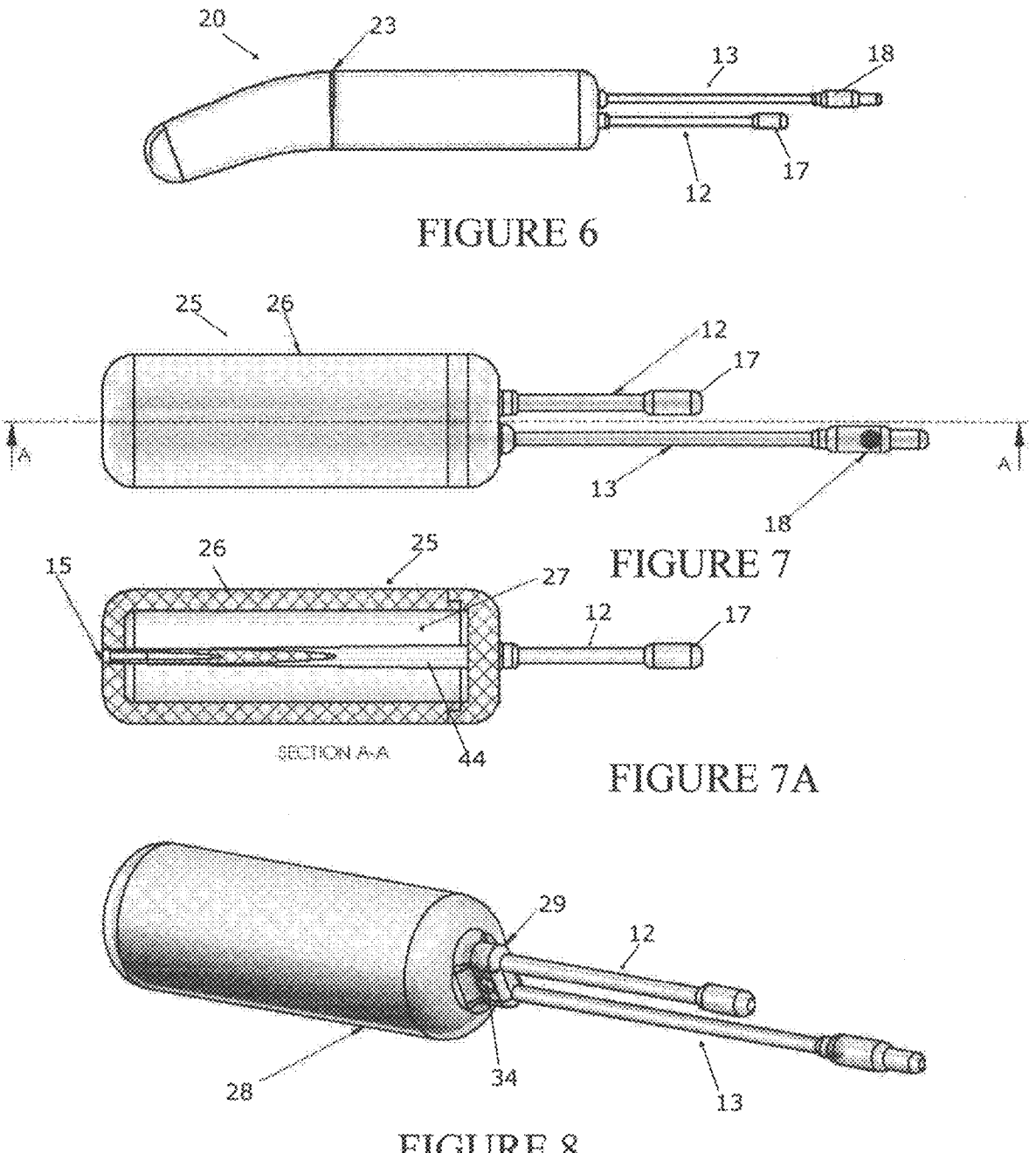
FIG. 6 is a lateral view of an embodiment of a form stable expandable stent of the invention.
FIGS. 7 and 7A are lateral and sectional views, respectively, of another embodiment of the form stable expandable stent of the invention.
FIG. 8 is perspective view of another embodiment of the form stable expandable stent of the invention.

Referring to FIGS. 6-8, form stable expandable stent embodiment 20 is shown to have curved and tapered body configuration 23 in FIG. 6. Fill tubing 12 and drainage/irrigation tubing 13 are shown in communication with tapered body 23. In FIG. 7, a vaginal stent structure 25 is shown whereby the exterior shell or body 26 of the device has thick silicone walls so that an interior foam structure is not required to maintain device form stability. FIG. 7A is a sectional view of the fill chamber 27, the molded silicone rubber shell body 26 as well as the drain/irrigation tube 12 extending through the device body 26 as shown by internal tube section 44. In FIG. 8, the expandable vaginal stent 28 is shown to have an integrated pull tab structure 29 with a thru hole 34 which allows for the attachment of a pull string for the removal of the device 28. The tab 29 structure is shown integrated between the device body and the tubing structures 12, 13.

FIGS. 9-10 show expandable stent assemblies having bodies with multiple chambers. In FIGS. 9 and 9A, an expandable stent device 30 is shown having an expandable body 31 with multiple chambers 32, 33. In the sectional view of FIG. 9A, the inner chamber 32 and the outer chamber 33 are shown to comprise the cylindrical body 31 of the device 30. FIG. 10 shows another embodiment 35 of the form stable expandable stent wherein the stent body is comprised of multiple chambers 36 and 37 which are in communication with fill tubing and ball valve assemblies 38 and 39, respectively. The multiple chambers shown in series allow a user to adjust each chamber to different pressures. By reducing the pressure on the anterior chamber 37, the insertion end is effectively reduced and the resultant more tapered structure provides easier insertion into the patient. Once the two chambered stent 35 has been placed inside the patient, the anterior chamber 37 can be expanded to provide a more bulbous end. The resultant increased diameter of chamber 37 aids in securing the device and reducing the likelihood of slipping out during routine dilation, for example.

Figures 12, 13, 13A, 14, 15:
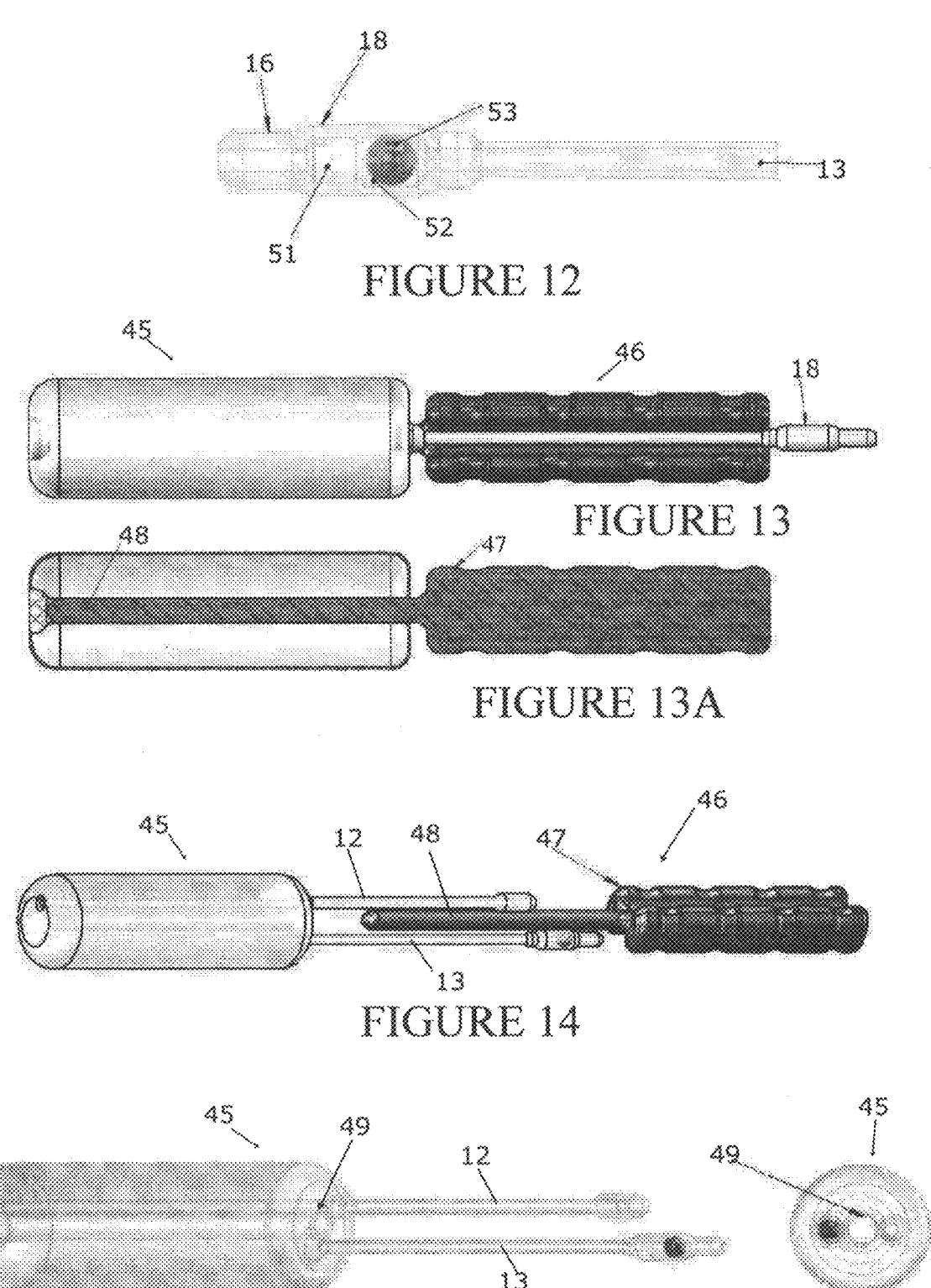
FIG. 12 is a lateral view of the valve of FIG. 11.
FIGS. 13 and 13A are lateral and sectional views, respectively, of another embodiment of the form stable expandable stent of the invention.
FIG. 14 is a perspective view of another embodiment of the form stable expandable stent of the invention.
FIG. 15 is a perspective view of another embodiment of the form stable expandable stent of the invention.

In FIGS. 11 and 11A, expandable vaginal stent 40 is shown having a fill chamber through which a reinforced drain/irrigation tube 42 extends. The reinforced tube 42 has gussets and buckle support ribs. FIG. 12 shows the ball check valve 18 at the end of the fill tube 13 in detail and wherein the valve structure is shown comprised of a sealing chamber 51 and an open chamber 52 having the stainless steel ball 53. The luer lock adapter 16 is shown extending from the ball check valve 18 at the terminal end of the fill tube 13.

The filling tube 13 utilized in the stent assembly is preferably sealed with a ball valve structure 18 that allows the user to connect a syringe to the valve structure to thereby easily fill and drain the device body for removal. As shown in the various drawing Figures and particularly in FIG. 12, the improved sealing and fluid flow capability of the ball valve structure 18 is provided by the utilization of two chambers 51 and 52. The first chamber 51 is used to seal the device and is generally smaller in diameter than the ball 53 whereas the second chamber 52 is larger in diameter than the ball 53 and has dimples in the upper four quadrants which are positioned to stop the ball from seating or sealing the device when the fluid flow force moves the ball to permit the fluid to pass through the second chamber.

The check valve is constructed to restrict fluid exiting the stent device while the user switches from an empty to a full syringe, for example. The check valve maintains fluid pressure unless squeezed between the user's fingers which deforms the valve body and allows fluid to drain. The check valve also restricts fluid from entering the stent device and keeps the coiled foam from self expanding subsequent the internal vacuum created when the coiled foam is compressed by the user prior to insertion of the device into the patient. The check valve has a second sealing chamber which securely locks fluid within the stent structure and thereby protects against accidental leakage, for example.

The size of the tubing utilized in the stent assemblies is dependent upon the size of the expandable stent structure. The drainage/irrigation tubing may also be reinforced with gussets and/or ribbing as well as by a mesh, coils or netting structures. The drainage/irrigation tube exit structure may also be provided with a manifold to distribute the fluid exchange.

Figures 16, 16A, 17, 17A:
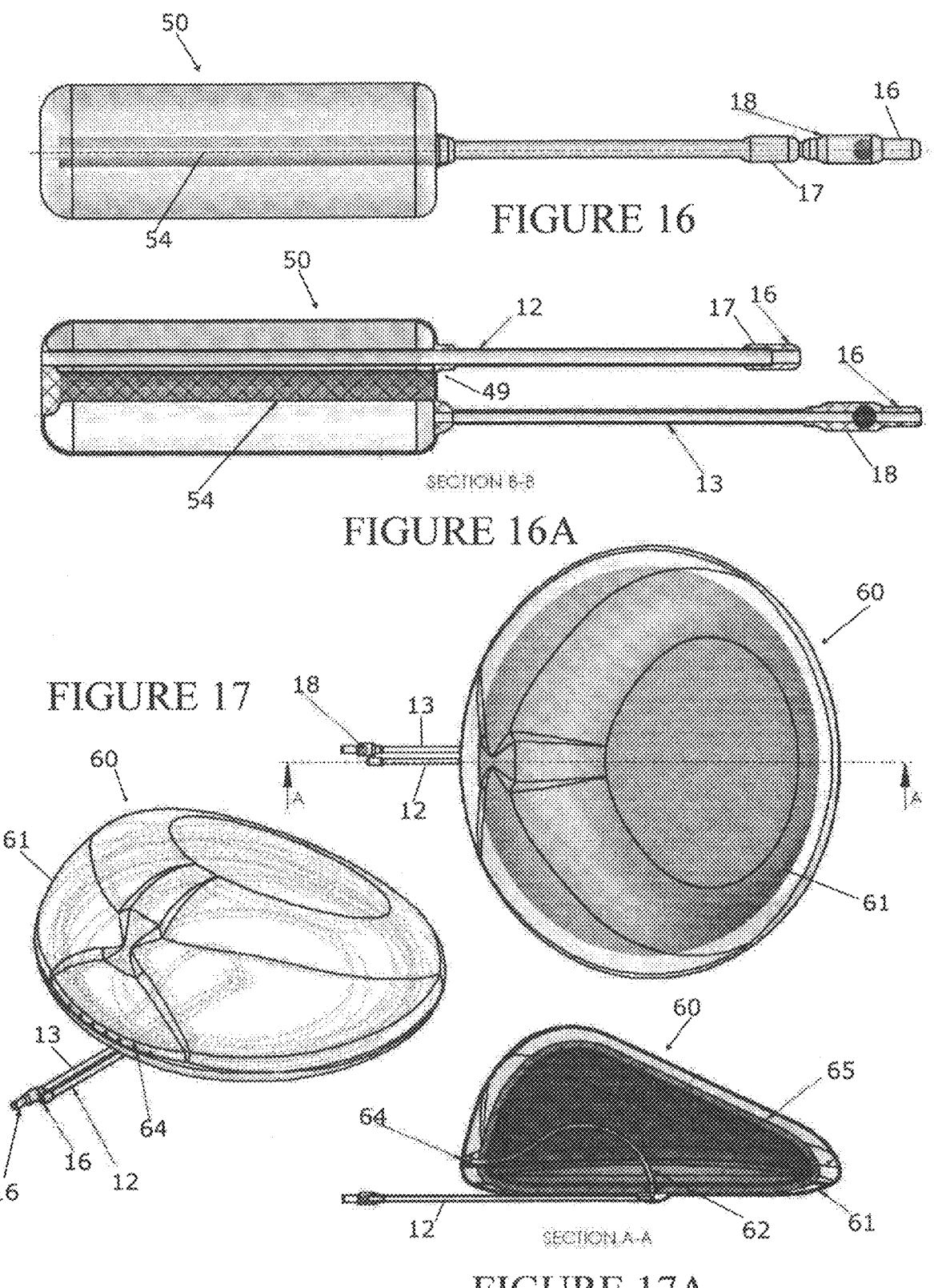
FIGS. 16 and 16A are lateral and sectional views, respectively, of another embodiment of the form stable expandable stent of the invention.
FIGS. 17 and 17A are perspective and sectional views, respectively, of various embodiments of the form stable tissue expandable devices of the invention.

Referring to FIGS. 13-16, the form stable expandable stent 45 is shown being utilized with a rigid handle structure 46 having a handle portion 47 for gripping and a directional center rod 48 for insertion into the center tube 54 of the cylindrical body of the expandable stent 45. The handle portion 47 is shown to have elongated exterior slots in which the fill tube 13 and drainage and irrigation tubing 12 may extend. As shown in FIG. 16, rigid center support 54 is shown extending through the fill chamber of the stent body 50. The directional rigid center rod structure may also be incorporated into the shell body for improved insertion capabilities as shown in FIGS. 16 and 16A. The directional handle structure 46 may be utilized for improved insertion and removal of the stent body.

Referring to FIG. 17, various shapes of the form stable tissue expansion devices are shown and which can be utilized in accordance with the teachings of the invention. For example, expandable assembly 60 may be utilized for breast reconstruction procedures and shown having a formed shell 61 with a silicone or foam interior 65 to provide form stability. As further shown, drainage and irrigation tubing 12 and fill tubing 13 are shown connected to the formed silicone shell body 61. In the sectional view the interior drain/irrigation tubing 62 is shown extending to tube exit 64.

Figures 18, 18A, 18B, 19, 19A:
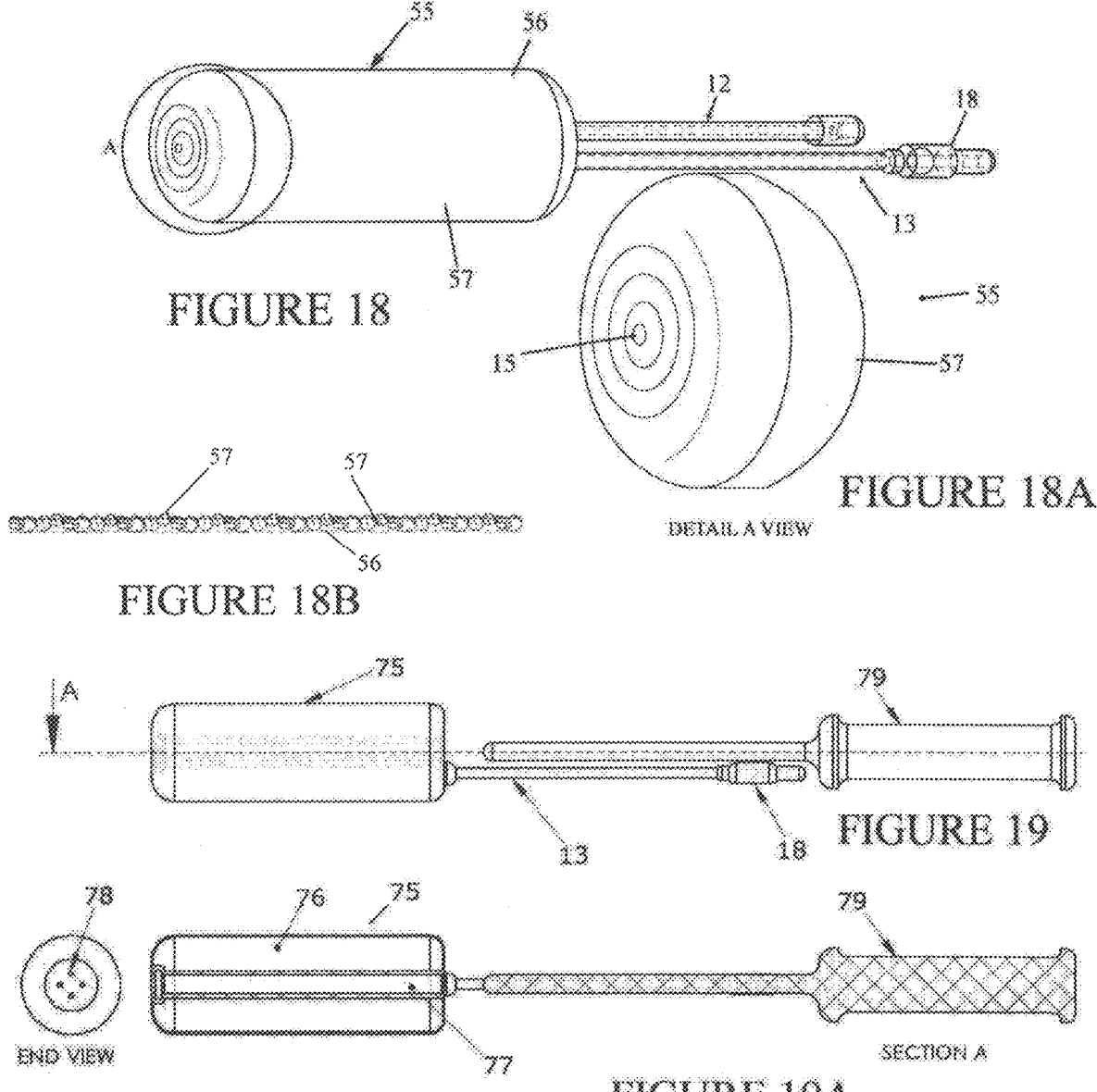
FIGS. 18 and 18A show perspective views of an alternate embodiment of the form stable expandable stent of the invention.
FIG. 18B is an enlarged view showing the textured surface of the shell body of FIG. 18.
FIGS. 19 and 19A are lateral and a sectional views, respectively, of another embodiment of the form stable expandable stent of the invention.

Referring to FIGS. 18 and 18A, an expandable stent 55 is shown having an exterior shell body 56 formed of a textured silicone 57 which may be provided to reduce encapsulation. Tubing 12 and 13 and tube exit 15 are shown. FIG. 19 shows a vaginal stent assembly 75 comprising an expandable cylindrical body with an integral drainage tube and handle insertion sleeve 77 extending through chamber 76. The assembly is further shown to have multiple offset drainage holes 78 and an insertion handle structure 79 is shown aligned with the insertion sleeve 77.

FIG. 18B shows the textured surface 57 of the shell body 56 and which may be provided between silicone layers during the liquid silicone dip casting process, for example, wherein silicone particulates 57 are added while the silicone layer is still tacky before vulcanization into a cured silicone rubber stent shell. Multiple layers could also be utilized. The silicone coating may be provided on one or more sides of the foam structure, as shown, for example, in FIGS. 22 and 22A. A foam composite may also be used to provide desired rigidity.

The textured surface of the stent may reduce friction between the tissue and the stent body and also reduces the risk of capsular contracture while the tissue graft is healing. The textured surfaced stent makes the stent device more easily and less painful to remove from the patient. The exterior surface further is hydrophobic in nature to avoid blood absorption and thus potential clotting and also easily cleaned and utilized in multiple dilation cycles.

Figures 20, 21, 21A, 21B:
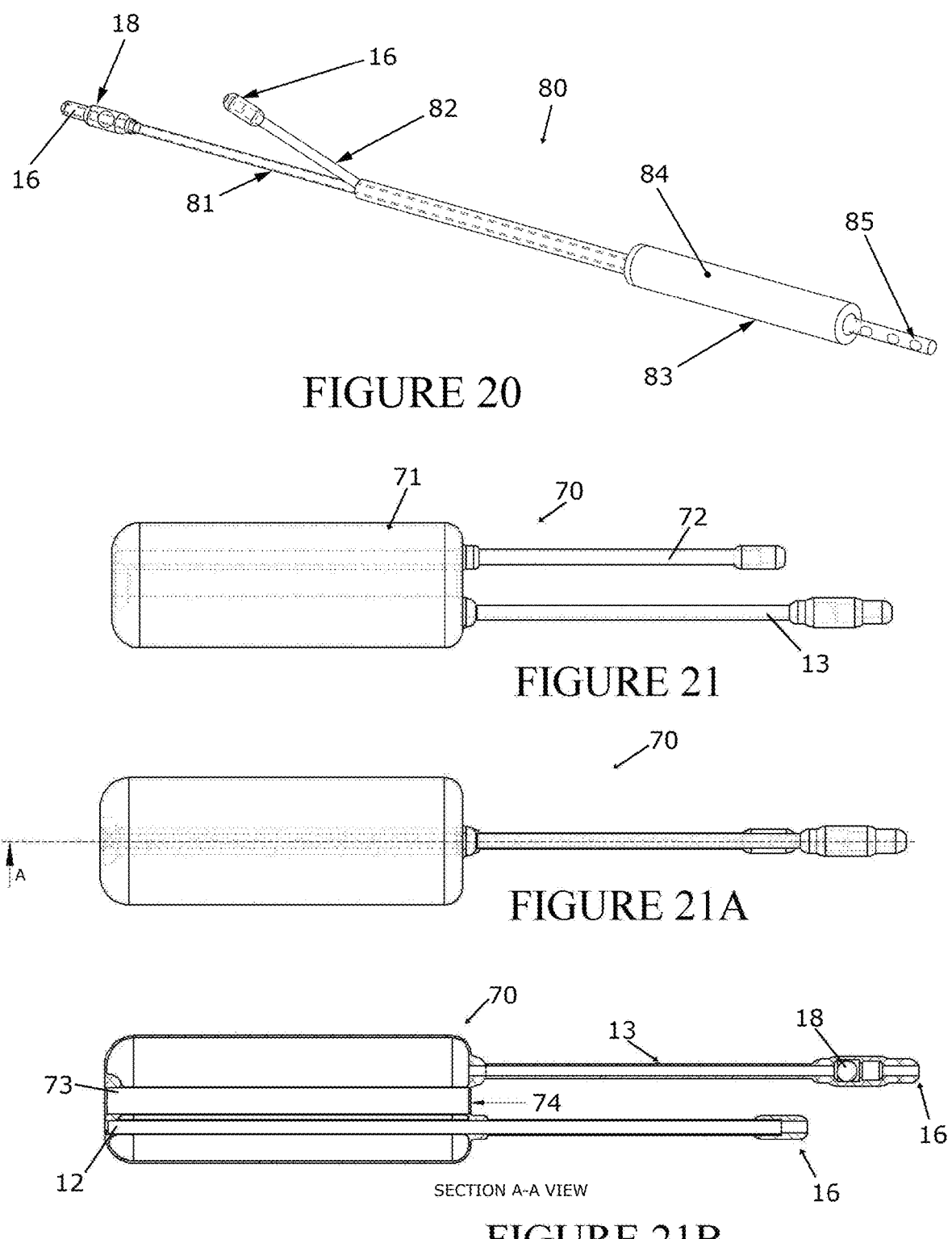
FIG. 20 is a perspective view of a form stable esophageal stent embodiment adapted for use in esophageal reconstruction and Nissen Fundoplication procedures.
FIGS. 21, 21A and 21B are top, lateral and sectional views, respectively, of a form stable expandable stent embodiment having multiple drain/irrigation tubing structures.

Referring to FIG. 20, a form stable expandable stent 80 is shown adapted to be utilized in esophageal reconstruction and Nissen Fundoplication procedures. The stent device 80 is shown having elongated cylindrical expandable shell body 83 with fill tubing 81 and drain tubing 82 with multiple hole drain 95. The esophageal form stable expandable stent 80 allows for the simplification and improved results for the specified surgical procedures. For example, the Nissen Fundoplication procedure has traditionally required the use of two devices: a first device used to deflate the stomach and the second device used to stent the esophagus. This two-step procedure can be tedious, time-consuming, vulnerable to mistakes and may be damaging to the esophagus. The form stable esophageal stent 80 is designed to consolidate the procedure into a one step procedure that is more efficient for the surgery and safer for the patient. The expandable open cell foam 84 within the esophageal device body 83 stabilizes the balloon dilation, allows the balloon to expand with air and not saline, thus reducing the filled device weight, reducing procedural time and overall improved surgical results.

Referring to FIGS. 21-21B, top, lateral and sectional views are shown of form stable expandable stent assembly

70. The stent assembly 70 is shown having multiple drain/irrigation tubing structures 12 and 13, the latter integrated in the center of the form stable stent body 71 to improve buckling resistance, while also improving cavity drainage as the patient is being irrigated. The irrigation tubing may be sized to maximize the fluid rate and pressure as the fluid is exiting the syringe. The centrally positioned separate drainage tube 73 has a larger diameter than the irrigation tube 12 to allow the air in the cavity to escape during irrigation and to ensure full drainage of the cavity, thereby minimizing the risk of septic shock.

Figures 22, 22A, 23, 23A, 24, 25:
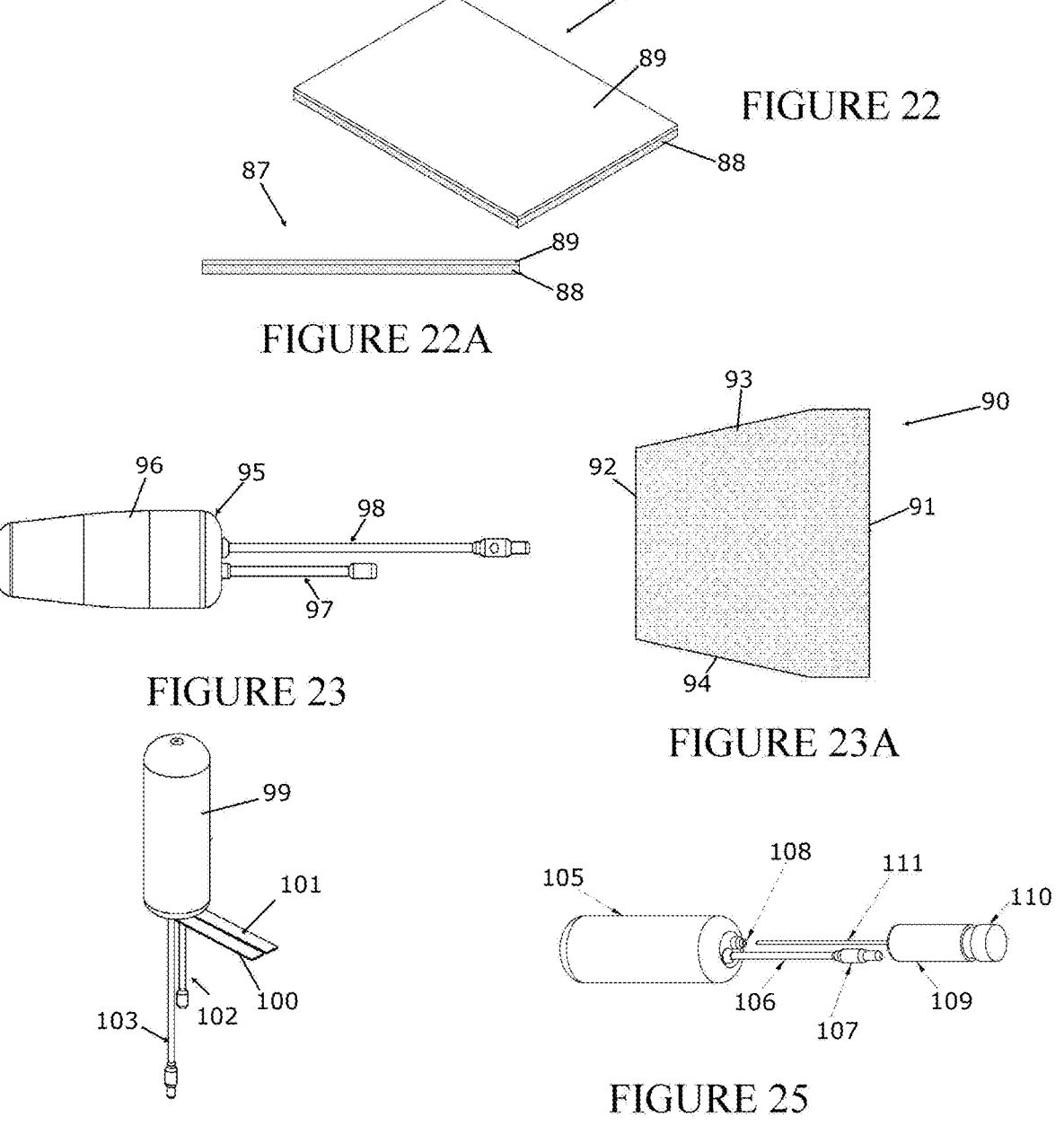
FIGS. 22 and 22A are perspective and lateral views, respectively, showing a layered foam structure of the invention.
FIG. 23 is a lateral view showing a tapered stent assembly of the invention.
FIG. 23A is a top view showing a foam structure having a predetermined shape for insertion into the stent assembly of FIG. 23.
FIG. 24 is a perspective view of a stent assembly having flexible strands.
FIG. 25 is a perspective view of another embodiment of the form stable expandable stent assembly of the invention.

FIGS. 22 and 22A are perspective and lateral views, respectively, showing the layered foam structure 87 having a silicone layer 89 on the foam structure 88.

The process to produce a form stable form expandable stent assembly may be as follows. The shell body may be formed of silicone and dip coated and vulcanized. The tubing junction is next heat vulcanized to the silicone shell body. The shell body having the integrated drain tube is next filled with the foam stabilizing structure. The device is then sealed with silicone sheeting using either a room temperature vulcanization (RTV) silicone adhesive or heat vulcanization. Reinforced suture tabs may next be adhered to the posterior side of the device with RTV silicone adhesive. Finally, the expandable stent assembly is cleaned, packaged and sterilized for medical use. The materials utilized in the structure of the form stable expandable stent assembly are biocompatible materials capable of being sterilized.

Referring to FIGS. 23 and 23A, a stent assembly 95 is shown having a tapered stent body 96 tapering downwardly from the body end having the drain/irrigation tube 97 and fill tube 98. FIG. 23A shows a layered foam structure configuration 90 having opposing sides 91 and 92 and tapered sides 93 and 94. The foam structure 90 when rolled into a coiled configuration, is placed within the tapered stent body 96 of the stent assembly 95. The tapered foam shape 90 provides a more even compression to the stent body 96. As shown, various foam shapes and sizes to align with corresponding form stable stent shapes may be similarly provided. The tapered or torpedo shaped form stable stent assembly 95 reduces the force required for insertion into the user and aid in patient compliance.

FIG. 24 shows stent assembly 99 having strands 100 and 101 extending from a terminal end of its body. The strands 100, 101 are preferably flexible and constructed of silicone sheeting reinforced by Dacron netting to provide tensile strength and to reduce the likelihood of tearing. The flexible strands provide a surgeon with means to secure a urethral catheter during surgery by eliminating the need for suturing; the flexible strands may be tied together and around a catheter during surgery. The flexible strands further aid the user to remove the stent device from the tissue pocket subsequent healing.

Another application of the form stable expandable stent of the invention is shown in FIG. 25 and which entails the use of a removable stylet assembly 109 to simplify the reinsertion of the stent assembly 105 and to allow the patient to continue routine dilation of the tissue for multiple durations after completion of the surgery. In order to avoid constriction of the tissue, dilation is critical to the patient's surgical success. Post surgical care of the form stable stent requires the patient to remove the stent device periodically for cleaning and re-insertion of the device. In order to assist the patient with post-surgical dilation, the form stable expandable stent assembly 105 may have the length of the drain tube 108 shortened or trimmed to allow for the amalgamation of a specifically designed insertion stylet 109 for the stent. This stent stylet assembly 109 is shown to incorporate a handle 110 and an insertion rod 111. The insertion rod 111 consists of a rigid material, such as stainless steel or similar material, and having an outside diameter small enough to glide easily inside the drain tube 108, which is integral to the form stable expandable stent assembly 105. The patient may slide the stent stylet 109 into the form stable expandable stent 105 to increase the rigidity during re-insertion. Once the device has been properly placed, the stent stylet 109 may be easily removed, allowing the form stable expandable stent to be comfortable inside the patient and supportive to the healing tissues during post-surgical dilation cycles.

As many changes are possible to the form stable expandable stent embodiments of this invention utilizing the teachings thereof, the descriptions above, and the accompanying drawing should be interpreted in the illustrative and not in the limited sense.

That which is claimed is:

1. A form stable expandable stent assembly comprising:
   an expandable flexible body having an exterior surface, an interior chamber, a first end and a second end;
   b) a form stable structure active on said flexible body, said form stable structure being a coiled foam structure positioned within said interior chamber of said flexible body, said foam structure having a layer of silicone;
   c) a filling tube in communication with said interior chamber and being connected at said first end of said flexible body; and
   d) an irrigation tube connected at said first end of said flexible body and extending through said interior chamber to said second end of said flexible body.

2. The form stable expandable stent assembly of claim 1, wherein said expandable flexible body is a silicone shell defined by a silicone wall, said silicone wall having a textured exterior surface.

3. The form stable expandable stent assembly of claim 1, wherein said filling tube and said irrigation tube have terminal ends and wherein a luer lock adapter is connected to said terminal ends of said filling and irrigation tubes, and further wherein said filling tube has a ball valve at its terminal end in communication with said luer lock adapter, said ball valve being a two-position check valve.

4. The form stable expandable stent assembly of claim 1, wherein said interior chamber has a centrally disposed sleeve extending from said first end to said second end of said expandable flexible body and wherein an elongated rod with a handle member is provided for insertion into said sleeve to maneuver and position said expandable stent assembly.

5. The form stable expandable stent assembly of claim 1, wherein said flexible body has a flexible tab structure attached at said first end, said tab structure adapted for suturing and stent assembly removal.

6. The form stable expandable stent assembly of claim 1, wherein a pull tab with a thru hole is attached at said first end of said expandable flexible body.

7. The form stable expandable stent assembly of claim 1, wherein said coiled foam structure has beveled edges.

8. The form stable expandable stent assembly of claim 1, wherein said predetermined shape of said flexible, walled body is an elongated cylindrical structure or a curvilinear structure and wherein a stylet assembly is provided having a handle and an elongated rod extending therefrom, said rod constructed for insertion into said irrigation tube to aid in maneuvering said expandable flexible body of said stent assembly.

9. A form stable expandable stent assembly comprising:
   a) a sealed expandable shell forming an internal chamber;
   b) a form stability member active in said internal chamber of said sealed expandable shell; said form stability member being a coiled foam structure positioned in said internal chamber;
   c) drainage/irrigation tubing extending thru and from said expandable shell; and
   d) a fill tube having a ball valve connected to said internal chamber, said ball valve being a two-position check valve.

10. The form stable expandable stent assembly of claim 9, wherein said drainage/irrigation tubing and said fill tube have terminal ends with luer lock adapters.

11. The form stable expandable stent assembly of claim 9, wherein said expandable shell has a centrally disposed sleeve extending therethrough and wherein a handle with a centrally disposed rod is provided for insertion into said sleeve to thereby permit said stent assembly to be maneuvered by means of said handle.

12. The form stable expandable stent assembly of claim 9, wherein a flexible tab structure is attached to an end of said shell for suturing and for assembly removal.

13. The form stable expandable stent assembly of claim 9, wherein an integrated pull tab having a thru hole is attached to one end of said shell.

14. The form stable expandable stent assembly of claim 9, wherein said coiled foam structure has beveled edges.

15. The form stable expandable stent assembly of claim 9, wherein said predetermined shape of said flexible, walled body is an elongated cylindrical structure or a curvilinear structure.

16. An expandable, form stable tissue expanding assembly comprising:
   a) a flexible, walled body having a chamber of a predetermined shape;
   b) a stability structure active on said walled body, said stability structure being an expandable coiled foam structure for expansion in said chamber of said flexible walled body;
   c) a fill tube in communication with said chamber of said walled body and extending from said walled body; and
   d) a drainage and irrigation assembly extending through said walled body and extending therefrom.

17. The expandable, form stable tissue expanding assembly of claim 16, wherein said fill tube and said drainage and irrigation assembly have terminal ends with luer lock adapters, and further wherein said fill tube has a ball valve structure said ball valve structure being a two position check valve.

18. The expandable, form stable tissue expanding assembly of claim 16, wherein said predetermined shape of said flexible, walled body and said predetermined shape of said coiled foam structure are similar shapes.

19. The form stable expandable stent assembly of claim 16, wherein said expandable foam structure has beveled edges and a silicone layer.

20. The form stable expandable stent assembly of claim 16, wherein said flexible body has a textured outside surface and further has a flexible tab structure attached thereto.

\*    \*    \*    \*    \*